United States Patent
Shipp et al.

(10) Patent No.: US 6,203,517 B1
(45) Date of Patent: Mar. 20, 2001

(54) MINIMIZATION OF TRANSPORT OF CANCER CELLS

(76) Inventors: John I. Shipp, 104 Short Springs Rd., Tullahoma, TN (US) 37388; Morris E. Franklin, Jr., 3242 E. South Cross Blvd., San Antonio, TX (US) 78222; Richard H. Klein, 16506 Strong Box, San Antonio, TX (US) 78247

(*) Notice: Subject to any disclaimer, the term of this patent is extended or adjusted under 35 U.S.C. 154(b) by 0 days.

(21) Appl. No.: 09/090,516

(22) Filed: Jun. 4, 1998

(51) Int. Cl.$^7$ .................................................. A61B 17/20
(52) U.S. Cl. ............................................. 604/22; 604/264
(58) Field of Search ............................ 604/27, 257, 259, 604/264, 265, 275, 523, 164, 22

(56) References Cited

U.S. PATENT DOCUMENTS

| | | | | |
|---|---|---|---|---|
| 4,186,745 | * | 2/1980 | Lewis et al. ........................... | 604/265 |
| 4,769,013 | * | 9/1988 | Lorenz et al. ......................... | 604/265 |
| 5,007,897 | * | 4/1991 | Kalb et al ............................. | 604/43 |
| 5,318,531 | * | 6/1994 | Leone .................................... | 604/96 |
| 5,344,411 | * | 9/1994 | Domb et al. ........................... | 604/265 |
| 5,383,928 | * | 1/1995 | Scott et al. ............................. | 623/1 |
| 5,628,760 | * | 5/1997 | Knoepfler .............................. | 606/170 |
| 5,688,239 | * | 11/1997 | Walker ................................... | 604/96 |

\* cited by examiner

*Primary Examiner*—Wynn Wood Coggins
*Assistant Examiner*—Deborah Blyveis
(74) *Attorney, Agent, or Firm*—Lucian Wayne Beavers Waddey & Patterson

(57) ABSTRACT

A surgical apparatus includes an instrument having an operative zone defined thereon for physical engagement with a patient's body tissue. The instrument has a foraminous outer shell disposed in the operative zone. The foraminous outer shell has a multitude of relatively uniformly dispersed, small perforations defined therein. The instrument has a fluid supply channel communicated with the perforations for diffusing a flushing fluid out of the perforations throughout the operative zone so that adhesion of tissue to the operative zone of the instrument is reduced. The flushing fluid preferably includes a cytotoxic solution and/or an anti-adhesive solution. Additionally, or alternatively, the outer surface of the instrument may be permanently coated with a cytotoxic material and/or an anti-adhesive material. This surgical instrument is preferably used in combination with surgical procedures which are designed to minimize the transport of viable cancerous cells to other locations within the patient's body. Such surgical procedures preferably are laparoscopic procedures. Preferably any resected tissue is bagged prior to removal from the surgical site. Preferably the surgical procedure includes intraperitoneal chemotherapy following removal of the resected tissue.

15 Claims, 5 Drawing Sheets

CANCER CELL METASTASES

MINIMIZATION OF THE NUMBER
OF EXFOLIATED CANCER CELLS

MINIMIZATION OF CANCER CELLS TRANSPORT EFFICIENCY

MINIMIZATION OF CANCER CELLS IMPLANTATION

MINIMIZATION OF TRANSPORT OF CANCER CELLS

BACKGROUND OF THE INVENTION

1. Field of the Invention

The present invention relates generally to apparatus and methods for use in surgical removal of cancerous tumors.

2. Description of the Prior Art

As early as 1885, Gerster reported that surgical treatment for cancer might actually result in further dissemination of the disease. *N.Y. Med. J.* 41: 233–6 (1885). Wexner, et. al., reported that tumor formation at port sites following laparoscopic colorectal surgery is common. However, recurrences have not been limited to the port through which the specimen was retrieved, indicating that laparoscopic specimen bags or "wound protectors" are not sufficient to protect against "seeding" of exfoliated tumor cells. *Brit.J.Surg.* 82: 295–8 (1995). Tumor recurrence within trocar sites strongly suggests that the laparoscopic surgery itself may contribute to the dissemination of tumor cells into the peritoneal cavity. Sugarbaker, *Surg.Endosc.* 10: 295–6 (1996). The potential for tumor cell exfoliation and seeding is not limited to laparoscopic techniques, however, and Umpleby, et. al. have shown that large numbers of apparently viable tumor cells can be retrieved from the lumen of the large intestine after surgical resection. *Brit. J.Surg.* 71: 659–63 (1984).

Surgical resection of tumors often involves extensive manipulation of the resected specimen and the surrounding tissues due to limited space and tactile response. This provides an increased opportunity for exfoliation of tumor cells, with subsequent spread of those cells to other sites.

Tumor-laden instruments may also deposit cells into incisions. Nduka, et. al., *Brit.J.Surg.* 81: 648–52 (1994). Malignant cells have been shown to collect on both open and laparoscopic surgical instruments. *Dis. Colon Rectum* 35: 238–42 (1992). Furthermore, passage of resected tissue through the incision may coat the wound with exfoliated, potentially malignant cells. Nduka, *Brit.J.Surg.* 81: 648–52 (1994). To decrease the number of cells seeded into the wound in this manner, impermeable bags have been used to isolate the resected specimen from the surrounding tissue before removing it through the surgical incision.

However, this technique only minimizes seeding at the site of specimen removal, while exfoliated cells may be transported to and deposited at other sites. To address this problem, intraperitoneal chemotherapy has been employed with some success. Sugarbaker, *World J. Surg.* 19: 235–40 (1995). Fisher, et al., reported that the most effective chemotherapy application would be to use the largest tolerable dose at the time of or before primary tumor removal. *Cancer Res.* 43: 1488–92 (1983).

Two mechanisms have been proposed whereby chemotherapy may reduce tumor cell implantation: (1) cytotoxic effects on the tumor cells themselves, and (2) slowing down the wound healing process, reducing tumor cell entrapment. Jacquest, et. al., *Wounds* 7(2): 40–47 (1995). Early postoperative intraperitoneal chemotherapy has been proposed because, as adhesions form, viable cancer cells are trapped in a fibrin bundle—excluding the chemotherapeutic agent from the region. Sugarbaker, *World J.Surg.* 19: 235–40 (1995). Early events in wound healing play a role in tumor cell implantation, as suggested by the fact that the frequency of tumor implantation in injured sites was shown to decrease over time after tumor cell presentation. Sugarbaker, et. al., reported that intraperitoneal delivery of the chemotherapeutic agent 5-fluorouracil increased the dosage that could be tolerated without adverse side effects, and produced fewer hematologic toxicity reactions than lower doses given by the intravenous route. 98: 414–21(1985).

Franklin, et al., "Prospective comparison of open versus laparoscopic colon surgery for carcinoma: Five Year Results", (1996) reported that no trocar site implantations nor wound implantations were found in 215 patients followed from June 1990 through March 1996 after laparoscopic colon surgery for carcinoma using the following measures: (1) bagging of specimens prior to removal, (2) washing the trocar with povidone-iodine prior to removal, (3) removing intra-abdominal fluid to prevent tumor-laden fluid from bathing the wound, (4) removing insufflated gas prior to trocar removal, (5) irrigating the skin and subcutaneous sites with povidone-iodine prior to closure, (6) taking special care to avoid chipping or direct handling of the tumor, and (7) wound closure at the trocar site immediately after surgery. These results indicate that no single measure is sufficient to prevent the spread of exfoliated cells after surgical resection, and that proper preventive measures require a combination of techniques designed to minimize exfoliation and attachment of tumor cells at other sites.

Additionally, the prior art includes irrigation devices having fluid flow passages designed for irrigation of a surgical site. Prior art references which relate generally to such apparatus include the following:

U.S. Pat. No. 4,747,820 to Hornlein, et al.
U.S. Pat. No. 5,125,910 to Freitas
U.S. Pat. No. 5,197,948 to Ghodsian
U.S. Pat. No. 5,607,391 to Klinger, et al.
U.S. Pat. No. 4,846,790 to Hornlein, et al.
U.S. Pat. No. 5,186,714 to Boudreault, et al.

Thus, it is seen that there is a continuing need for improved apparatus and methods for minimizing the recurrence of cancerous tumors after cancer surgery.

SUMMARY OF THE INVENTION

The present invention provides surgical instruments and methods designed to minimize the implantation of viable cancerous cells and thus reducing recurrence of the disease.

One preferred embodiment of such an apparatus includes an instrument having an operative zone defined thereon for a physical engagement with the patient's body tissue. The instrument has a foraminous outer shell disposed in the operative zone. The foraminous outer shell has a multitude of small perforations, defined therein. The instrument has a fluid supply channel defined therein and communicated with the perforations for diffusing a flushing fluid out the perforations throughout the operative zone, so that adhesion of tissue to the operative zone of the instrument is reduced.

In another aspect of the invention, the flushing fluid contains a toxic fluid which kills cancerous cells which come in contact with the flushing fluid. This further reduces the presence of viable cancer cells which can be transported by the instrument and reduces the number of viable cells that may have reached an implantation site by other transport means.

In another aspect of the invention, the flushing fluid contains an anti-adhesive surfactant solution which further reduces adhesion of cancerous cells to the outer surface of the instrument and renders sites less susceptible to implantation.

Methods of using such apparatus are also provided.

It is therefore an object of the present invention to provide apparatuses and methods which reduce the transport of viable cancer cells by the instrument.

Another object of the present invention is the provision of surgical apparatuses and methods wherein the operating field is flushed with fluid containing a cytotoxin which kills the cancerous cells.

Still another object of the present invention is the provision of apparatuses and methods wherein an anti-adhesive surfactant is diffused through the surface of a surgical instrument thus flushing the surface with solution which inhibits the adhesion of cancerous cells to the instrument.

Still another object of the present invention is the provision of apparatuses and methods wherein an anti-adhesive surfactant is diffused through or applied to the surface of a surgical instrument thus flushing potential implantation sites which inhibits adhesion of cancerous cells to the site.

Yet another object of the present invention is the provision of surgical techniques which utilize apparatuses and methods like those just described in combination with other techniques which reduce the recurrence of cancerous tumors.

Still another object of the present invention is to provide means for minimizing the risk of implantation of viable exfoliated cancer cells during laparoscopic or open surgery.

Numerous other objects features and advantages of the present invention will be readily apparent to those skilled in the art upon the reading of the following disclosure when taken in conjunction with the accompanying drawings.

DETAILED DESCRIPTION OF THE PREFERRED EMBODIMENTS

Figure 1:
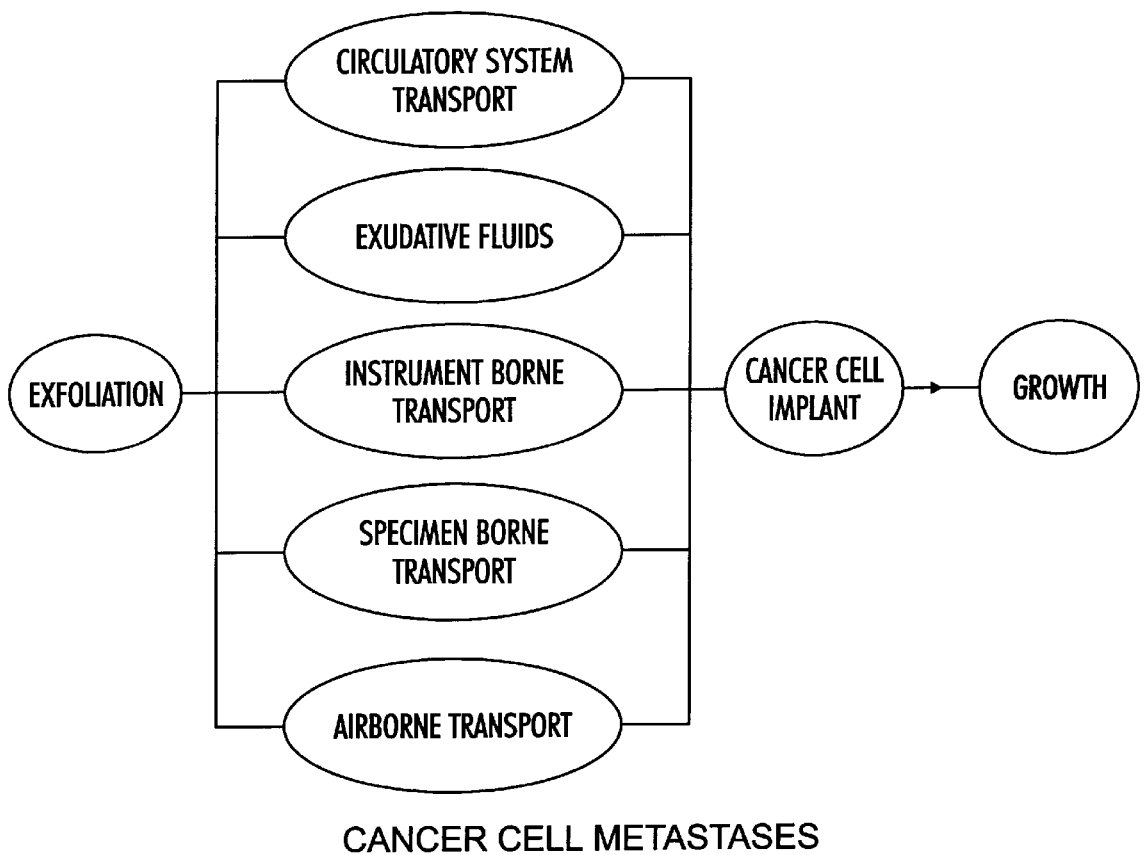
FIG. 1 is a schematic representation of the various mechanisms for cancer cell metastases.

The recurrence of cancer following surgical tumor removal is all too well known. Many varied mechanisms by which the metastases proceeds are well documented in the literature. A simplified view is that viable cancer cells become dislodged from the tumor, are transported to other sites in the body, and become implanted in these alternate sites that support their growth into a full blown secondary tumor. The chance of a secondary tumor forming is effected by the number of viable cells exfoliated, the efficiency of the transport mechanism, as well as the affinity for and the growth factors available at the alternate site.

Exfoliation seems to occur as a natural progression of a developing tumor. The number of viable exfoliated cells available for transport is related to the type, size, and location of the primary tumor. Exfoliation is also known to occur as a result of surgical manipulation during resection procedures. Viable exfoliated cells that happen to come into contact with favorable implant sites adhesively attach to the site where replication and growth occurs. Favorable sites include soft tissue organs such as the brain, liver, bone or lungs, resection suture or staple lines and surgical entry wounds.

Laparoscopic surgical procedures have become popular during the past few years owing to the shortness of hospital stay, the lessening of pain, and decreased scaring. Results for laparoscopic gall bladder removal have been so encouraging that in excess of ninety five percent of these procedures are now performed using this less invasive technique. Access to the abdominal cavity is provided through small puncture wounds (5 to 10 mm) using port devices called trocars. These allow the procedure to be accomplished by the insertion of tiny video cameras and small surgical instruments through the trocars while viewing the surgical field on a TV monitor. This method eliminates the larger wounds required in the case of the open procedures and the complications associated therewith and may offer other benefits to the patient.

The implant of viable cancer cells during laparoscopic surgery is a particularly disturbing problem since such implants may result in the death of the patient within a few months. Sugarbaker, *Surg. Endosc.* 10: 295–296 (1996), reports numerous incidences of trocar site cancer cell implants during bowel resections and gall bladder removal where unsuspected cancer was present. The rate of trocar site implants have caused some surgeons to suggest discontinuation of laparoscopic bowel resections, in spite of the otherwise obvious advantages of this less invasive technique.

It is well documented in the literature that recurrence of cancer in other sites often follows surgical removal of the primary tumor. Recurrence is found in sites throughout the body including soft tissue organs, lymphatic system, resection sites, areas within the abdominal cavity, and wound closure sites. The mechanisms for the metastases in the case of other organs and the lymphatic system may be through the transport of exfoliated cancer cells through the circulation systems. Occurrences in the abdominal cavity, the resection site of the bowel, and wound sites occur most frequently via a more direct mechanism.

The efficiency of cancer cell growth in various systems of the body has been demonstrated by Sugarbaker, *World J. Sure.* 19: 235–40 (1995). He injected 10 million viable tumor cells intravenously into littermate animals and found, on the average, 10 tumor growths in the lungs. Portal venous injection of the same number of cells resulted in only one tumor, on average, while intraperitoneal injection resulted in 1000 tumors. It is thus seen that the liver plays an important roll in destroying cancer cells in the hematogenous system. Sugarbaker reports that in a patient with large primary colon cancer, billions per day of viable cancer cells are destroyed by the liver. Thus few viable cells are available to invade the lungs, for example. On the other hand, direct peritoneal exposure resulted in 1 implant for each 10,000 viable cancer cells. This, and the timing of development of the abdominal, resection line, and wound site recurrence are strong evidence that the implant mechanism is a direct one, as opposed to the circulation system. This agrees with the conclusions of Nduka, et al., *Brit. J. Surg.* 81: 648–52 (1994).

Nduka, et al., suggest that one or more of three mechanisms are responsible for trocar site implants, airborne exfoliated cells carried to the trocar site via $CO_2$ pneumoperitoneum, direct contact of the removed specimen with the trocar wound, or direct contact of cancer cell laden instruments with the wound. To those suggested mechanisms we would add that of direct contamination by exudative fluid.

To avoid direct contact of the trocar wound with the resected specimen it has become accepted practice to bag the specimen prior to removal. Since there are reported incidence of trocar wound implants at the umbilical site with gall bladders that were found to contain very early stage cancer evolvement, the use of the bag technique is now common by some surgeons.

It is felt that the chance of a viable cancer cell which comes into contact with a wound becoming implanted is about 1 in 5000. This is derived from the number of viable exfoliated cells found in the extremes of resection specimen by Umpleby, et al., Brit. J. Surg. 71: 659–663 (1984) and the work by Sugarbaker, World J. Surg. 19: 235–40 (1995). Given this probability, the transport of the required number of viable cells from the resection site to a trocar wound via airborne transport is highly unlikely. It has been found, however, that laparoscopic instruments used in resections are often heavily laden with viable cells. Also, exudative fluids provide a very favorable environment for maintaining the viability of cancer cells over a long period of time. Cells can be transported by these peritoneal fluids to wound and resection sites, deposited into the growth factor rich environment of a trocar wound, for example, and become implanted.

What is needed then is means for minimizing exfoliation, means for minimizing or eliminating the transport modes and means for minimizing or eliminating adherence of the exfoliated cancer cells to alternate sites so that the possibility of implants of viable cancer cells during laparoscopic and open procedures is significantly reduced.

FIG. 1 depicts the mechanisms for cancer cell metastases. Cells are exfoliated, either by natural progressions of the tumor growth or surgical manipulation. These cells are then transported by either 1) circulatory means, the blood or lymphatic system, 2) peritoneal fluids such as exudate, 3) cancer cell laden surgical instruments used for the resection, or 4) the specimen as it is removed from the body coming into contact with body surfaces or 5) it has been suggested in the case of laparoscopic surgery, airborne transport via the $CO_2$ use for pneumoperitoneum is a potentially significant transport mode. The later mode is unlikely owing to the fluid environment, the affinity of the cancer cells for body tissue and instrument surfaces, and the specific gravity of the cells.

Figure 2:
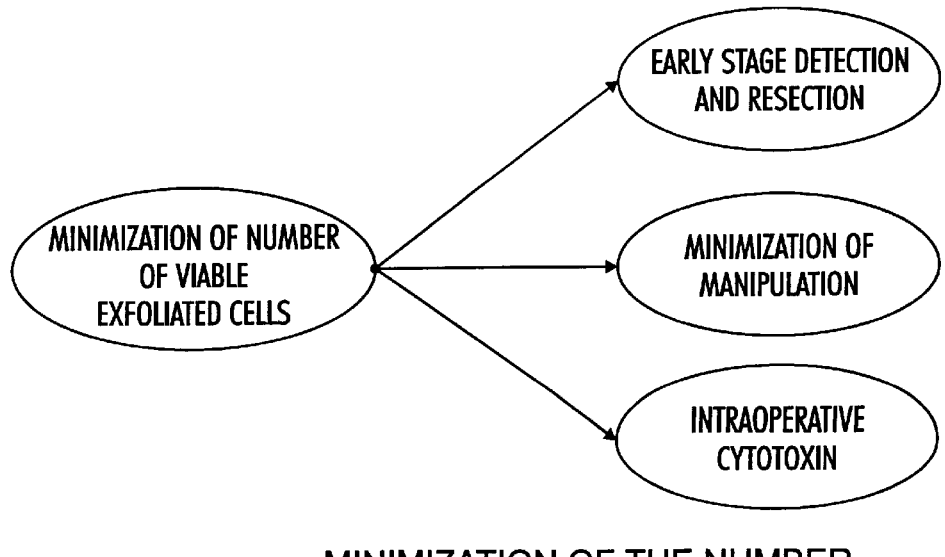
FIG. 2 is a schematic representation of various means by which the number of exfoliated cancer cells can be minimized.

FIG. 2 points out the means by which the number of exfoliated cells can be minimized. Early detection and resection while the tumor is smaller and is in a low class of development (Stage I or early Stage II) is well known to have a positive influence on recurrence rate. The minimization of surgical manipulation will, on average, result in fewer freed cells. Additionally, the use of an intraoperative cytotoxin, such as a Betadine solution lavage will minimize the number of viable exfoliated cells.

Figure 3:
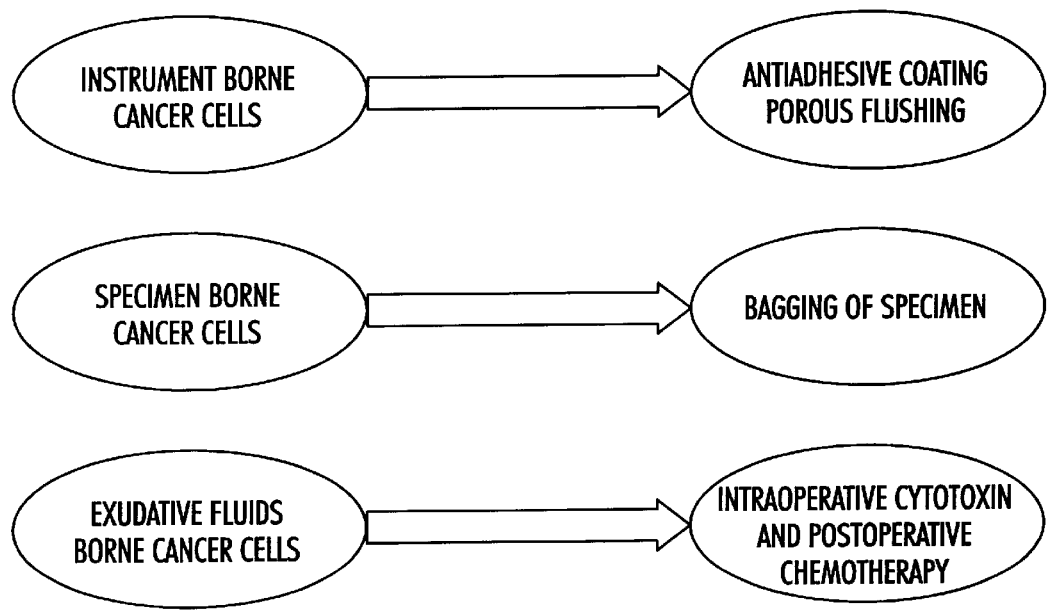
FIG. 3 is a schematic representation of various means for minimizing cancer cell transport efficiency.

FIG. 3 depicts the means for minimizing transport efficiency (non circulatory). The instruments should be anti-adhesive coated or designed of porous material that will allow flushing to remove otherwise adhering cells. Specimen to be removed from the body should be bagged at the resection site prior to removal. This is particularly important in laparoscopy. Exudative fluids provide a fertile environment for exfoliated cancer cells. The use of intraoperative cytotoxic lavage in the abdominal cavity, for example in the case of bowel resections will minimize liquid transport of viable cells.

Figure 4:
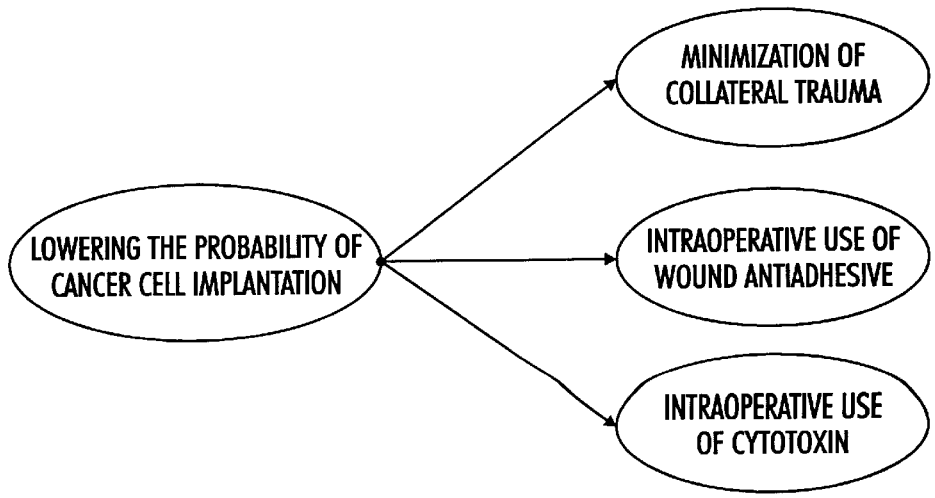
FIG. 4 is a schematic illustration of various means for minimizing cancer cell implantation.

FIG. 4 illustrates means for minimizing implants once exfoliation and transport has begun. Minimization of collateral trauma will allow for fewer favorable sites. Additionally, irrigating the wounds and trauma sites with anti-adhesive surfactant agents will dislodge implanted cells on which cytotoxins can react.

It is well known in the literature that many compounds destroy viable cancer cells. Chemo therapy drugs such as 5-Fluorouracil (5-FU) are often used postoperatively as an effective intraperitoneal cytotoxin, the direct action of which destroys large numbers of cancer cells. In addition, the use of a Betadine solution lavage, intraoperatively, has resulted in a very low recurrence rates.

There have been a number of studies that show that the earlier chemo treatment is administered, the more effective it becomes (Fisher, et al., Cancer Research 43: 1488–92 (1993)). Wound and surgical trauma supply growth factors for viable cells that are transported to these sites. The cells adhere to the wound via specific interactions with the wound matrix. These cells can not be easily dislodged with distilled water irrigation, Jacquest, et al., Wounds 7(2): 40–47 (1995).

Figure 5:
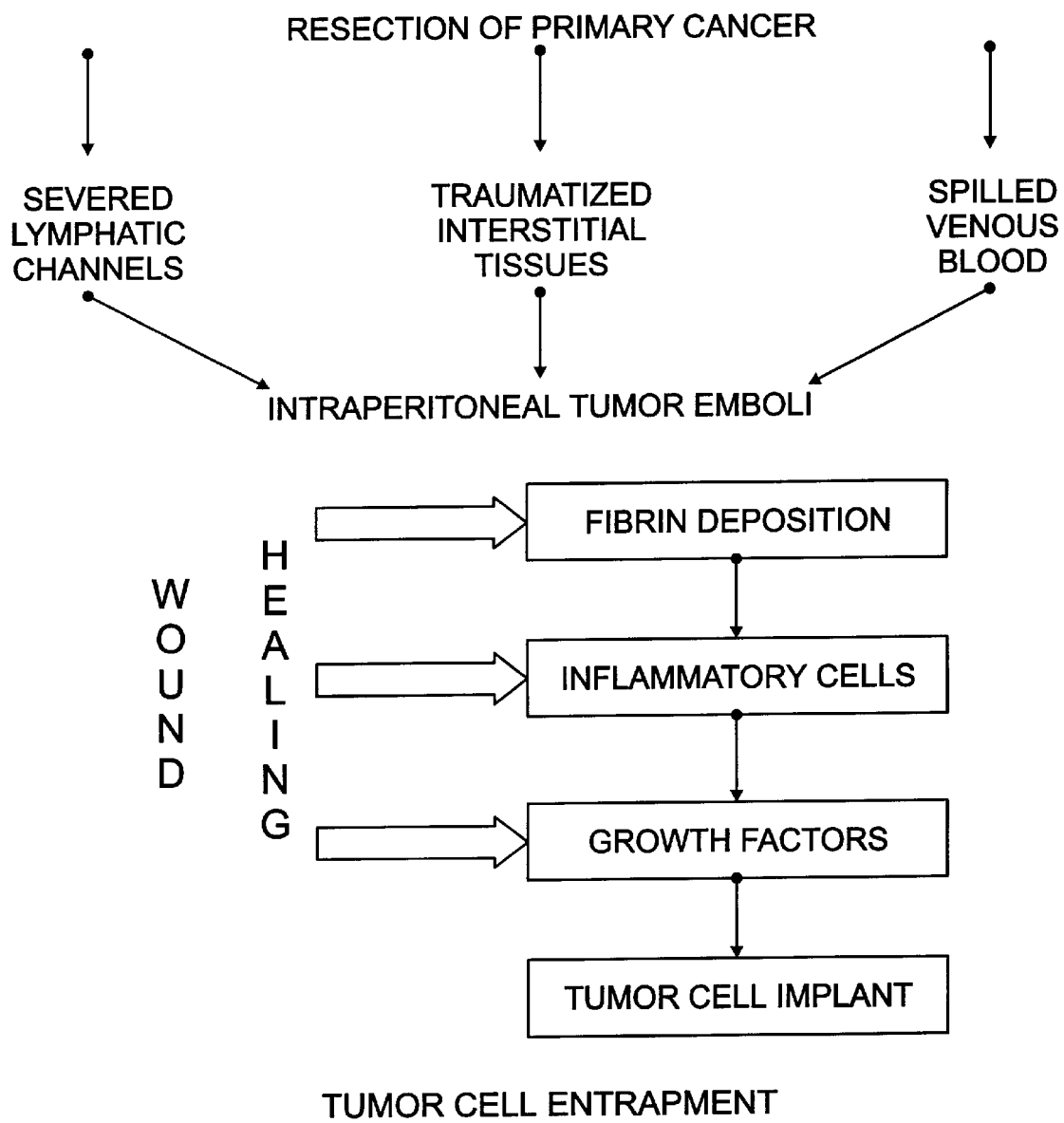
FIG. 5 is a schematic representation of the mechanisms of tumor cell entrapment.

The healing process in a wound that has been implanted gives rise to tumor cell entrapment in rapidly forming insoluble fibrin deposits and adhesions that excludes the direct contact of the chemo drug with the cancer cells. FIG. 5 is a diagram of the entrapment process as described in the Jacquest, et al., article.

Accordingly, we have concluded that an improvement would be provided by flushing the surgical site with cytotoxic fluid during the operation before wound healing processes have time to bind up the cancerous cells via fibrin encasement.

We have concluded that a preferred regimen for minimizing recurrence of cancerous tumors after surgery includes a surgical procedure which includes seven basic aspects, as follows.

The first step in an abdominal surgical procedure for minimizing the probability of implants is for the surgeon to minimize the collateral trauma both at the entry wound site(s) and in the operating field. Laparoscopic wounds are far less invasive than open wounds and, therefore, offer less wound implant area. Open procedures, on the other hand, allow more space, better visibility, and larger extraction space which would tend to decrease the number of exfoliated cells. Clearly, laparoscopy surgery performed by highly skilled laparoscopy surgeons who are able to resect tumors with minimal manipulation and collateral tissue damage would be desirable over open surgery, other procedural matters being equal.

The second step for minimizing implant probability is the use of an intraoperative cytotoxin to destroy any exfoliated cells in the operating field. This can be accomplished by creating a cytotoxin peritoneal lavage comprising, for example, a ten percent solution of Betadine applied through a standard irrigation/suction system at a flow rate, preferably, less than 1 liter per minute.

The third step is to avoid cancer cells from collecting on instrumentation that might come into contact with wounds and other trauma areas by providing constant flushing means for the instruments, by coating the instruments with a cytotoxin, iodine, for example, or to coat the instruments with antihesive means such as Teflon.

The fourth step in minimizing implants is the dislodging and/or destroying of any cells that may have reached the potential implant site. As discussed above, the healing process of a wound begins quickly with the clotting of blood from the blood vessels creating insoluble fibrin deposits. Any cell finding its way to the wound prior to the completion of the fibrin deposit process has a chance of becoming trapped beneath the deposit owing to the durability of the cell, protein stroma interface, and the protection provided by the fibrin build up. Hypotonic irrigation solution will not destroy the cells because of the insolubility of the fibrin and hydrostatic forces of surgical irrigation systems are inadequate to dislodge the attached cells, as described in Jacquest, et al., *Wounds* 7(2): 40–47 (1995).

The fifth step in the minimization process is the careful bagging of the specimen prior to removal to avoid direct contamination of the entry wound with the specimen, particularly in laparoscopic cases.

The sixth step in minimizing implants from abdominal access procedures is the use of an intraperitoneal chemotherapy regimen such as 5-fluorouracil (5-FU) as described in Sugarbaker, et al., *Surgery* 98(3) (1995).

The seventh step is to close all trocar site wounds immediately as described in Franklin, et al., Seminars in Colorectal Surgery (1994), the details of which are incorporated herein by reference.

Surgical Instruments with Flushing Means

Turning now to FIGS. 6–10, various embodiments of surgical instrument apparatus specifically designed to minimize transportation of viable cancer cells during a surgical operation are disclosed.

Figure 6:
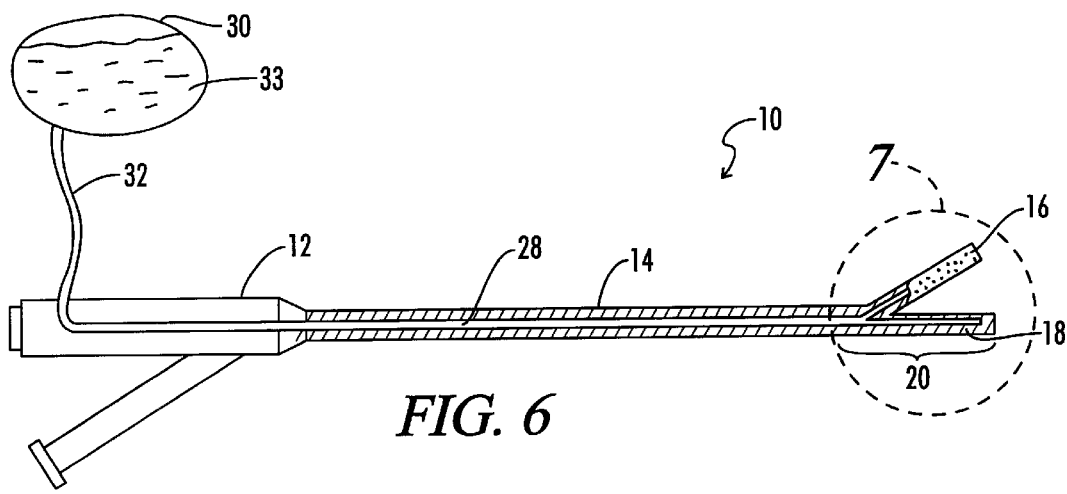
FIG. 6 is a schematic illustration of one particular type of surgical instrument, namely a grasper, having a porous outer shell with flushing system.

FIG. 6 shows a surgical instrument 10 of the type known as a grasper. The instrument 10 includes a handle 12 which is held by the surgeon. The handle 12 is attached to an elongated shaft 14. At the operative end of shaft 14 are a pair of articulated fingers 16 and 18 which can be moved together and apart in a scissors like fashion to grasp appropriate portions of the patient's tissue during a surgical operation in a known manner.

When the fingers 16 and 18 are closed together, the instrument 10, which is a laparoscopic instrument, can be inserted through a trocar having a diameter of no more than twelve millimeters, and preferably no more than five millimeters. The smaller the puncture site, the less trauma there is for the patient.

That portion of the instrument adjacent the grasping fingers 16 and 18 which is primarily subjected to physical engagement with the cancerous tissue being resected from the patient's body may be generally described as the operative zone 20 of the instrument 10.

Figure 7:
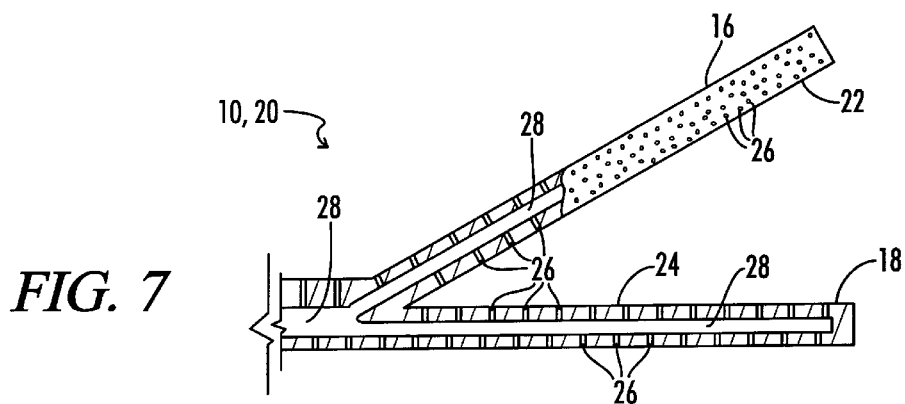
FIG. 7 is an enlarged view of the operative zone portion of the apparatus of FIG. 6.

FIG. 7 is an enlarged view of the operative zone 20 of instrument 10. The fingers 16 and 18 include a foraminous outer shell 22 and 24, respectively, defining outer surfaces thereof.

The outer shells 22 and 24 are foraminous outer shells having a multitude of perforations such as 26 relatively uniformly dispersed across the outer surface of the shell.

In one embodiment, the perforations 26 may be laser drilled holes in stainless steel shells 22 and 24. In that example, the perforations 26 would preferably have a diameter in a range of from 0.5 micron to one hundred microns. More generally speaking, the perforations 26 each have a diameter less than one-hundredth of a minimum cross sectional diameter of either of the grasping fingers 16 or 18. The perforations 26 are preferably very dense and located as close together as can practically be accomplished while still maintaining the structural integrity of the instrument.

In another embodiment the shells 22 and 24 could be made from a naturally porous material, such as a sintered ceramic material. Both the stainless steel and ceramic shells may be described as rigid shells.

The instrument 10 includes a fluid supply channel 28 defined therein which is communicated with a flushing fluid container 30 by a fluid conduit 32.

Each of the perforations 26 is communicated with the fluid supply channel 28 so that a flushing fluid 33 from the container 30 is diffused out the perforations 26 throughout the operative zone 20 of the instrument.

The flushing fluid 33 is provided from container 30 either under gravity flow or pressurized as necessary.

The flushing fluid 33 is provided from container 30 at a pressure which is sufficient, given the size and density of the perforations 26, such that the pressure of the flushing fluid 33 through the multitude of perforations 26 is sufficient to dislodge a majority of the cancer cells which would otherwise be adhered to the outer surfaces 22 and 24 of the operative zone 20 of the instrument 10. For example, using the laser drilled stainless steel shells described above, a flushing fluid provided at a pressure of from five to ten psi is believed to be adequate.

With the appropriate close spacing of many very small perforations, as in the examples described above, substantially the entire surface of the operative zone 20 will be wetted by flushing fluid flowing out of the perforations 26, so that substantially the surface of the entire operative zone will be flushed to wash away tissue which might adhere thereto.

The goal of minimizing the adhesion of viable cancer cells to the operative zone 20 of instrument 10 can be further achieved by use of preferred flushing solutions 33.

For example, the flushing fluid 33 may include a toxic fluid which kills cancerous cells. One example of such fluid is iodine, such as a 10% solution of Betadine. This reduces the adhesion of viable cancerous cells by killing the cells so that even if they adhere to the instrument, they are no longer viable.

Another form of flushing solution which operates in a different manner to minimize the adhesion of viable cancer cells is the use of a flushing fluid 33 which includes an anti-adhesive surfactant solution which reduces adhesion of cancerous cells to the outer shells 22 and 24 and to potential implantation sites. For example, such an anti-adhesive surfactant solution may include RGD peptide.

In addition to, or as an alternative to the provision of a flushing fluid as just described, the adhesion of viable cancer cells to a surgical instrument can be reduced by the provision of a permanent outer surface treatment which includes toxic materials and/or anti-adhesive materials.

For example, the outer surfaces 22 and 24 of the instrument in the operative zone 20 thereof may be coated with a cytotoxic coating such as one which includes iodine. Also, the outer surfaces 22 and 24 within the operative zone 20 may be coated with an anti-adhesive coating such as for example the material commonly referred to as Teflon, which is also known by the technical name tetrafluroethylene fluorocarbon polymer.

Figure 8:
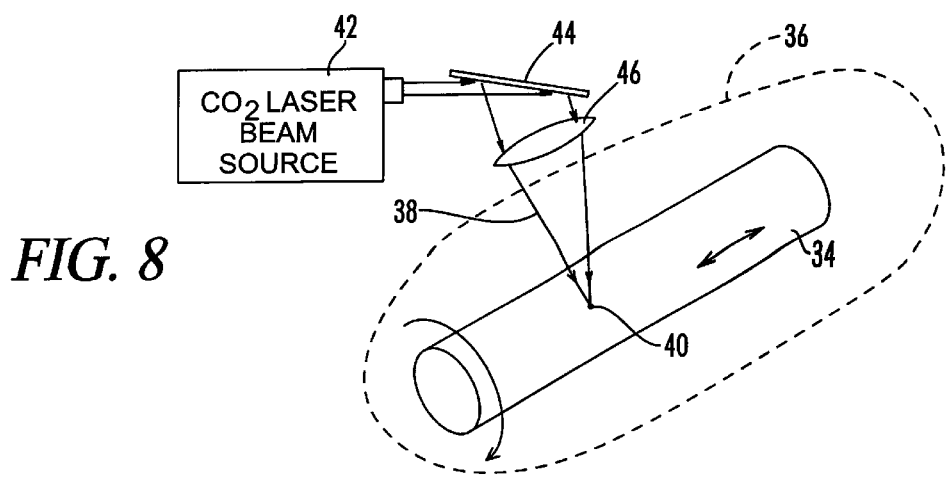
FIG. 8 is a schematic illustration of a preferred means for coating the exterior surface of an instrument with a cytotoxic material utilizing a laser.
Figure 9:
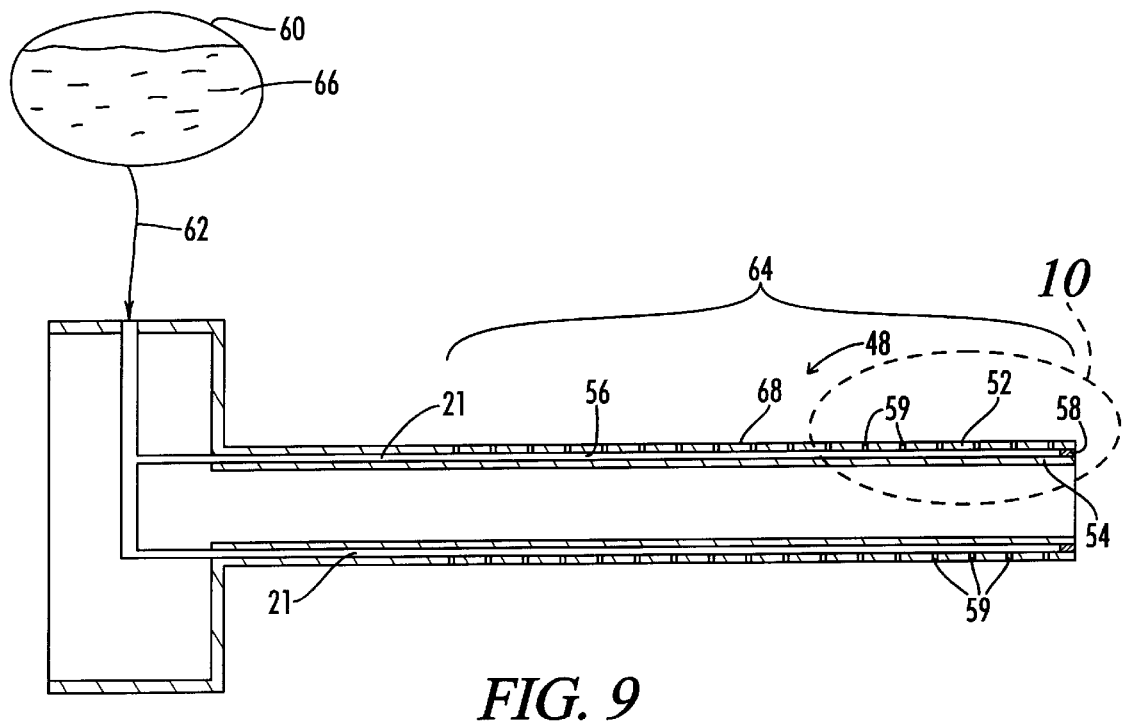
FIG. 9 is a schematic illustration of a trocar embodying the surface flushing system of the present invention.

For example, FIG. 8 schematically illustrates a preferred manner in which a surgical instrument 34 may have its outer surface coated with a toxic material such as iodine. Instrument 34 could be any type of surgical instrument, including the grasper 10 of FIG. 6, or the trocar 48 of FIG. 9.

First, the instrument 34 has its outer surface coated with iodine, such as for example by dipping the instrument in a liquid solution containing iodine.

Then the instrument 34 is placed within an inert gas shroud 36.

A laser beam 38 is then focused upon the outer surface of instrument 34 such as at focal point 40 to melt the coating on to the surface of the instrument.

The laser beam 38 is provided from a source 42 and is directed by mirror 44 through focal lens 46 to focus the same at focal point 40 on the surface of instrument 34. The laser 42 is preferably a $CO_2$ laser. The instrument 34 may then be rotated and translated relative to focal point 40 so that the entire outer surface of instrument 34 is treated by the laser. The general method of use of the $CO_2$ laser is described in Manohar, et al., "Production of Fe-Noble Metal Surface Alloys Using Laser Beams", *Journal of Laser Applications*, Volume 7, Pages 219–223 (1995), the details of which are incorporated herein by reference.

Figure 10:
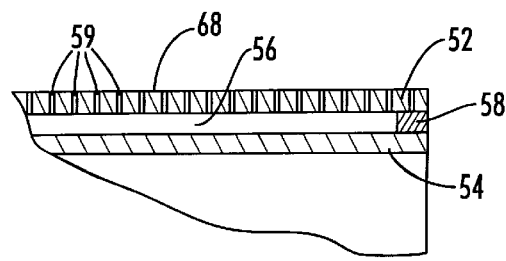
FIG. 10 is a enlarged view of an end portion of the trocar of FIG. 9.

FIG. 10 illustrates the application of the principals of the present invention to a different type of surgical instrument 48 known as a trocar. A trocar is a short tubular instrument which is placed through a small incision or perforation in the patient's skin to provide access to the abdominal cavities. Surgical instruments such as the instrument 10 of FIG. 6 are inserted through an inner bore 50 of the trocar to perform surgical techniques within the abdominal cavity.

In accordance with the present invention, the trocar 48 has an outer cylindrical shell 52, and an inner cylindrical shell 54 defining an annular fluid supply channel 56 therebetween. The end of the annular channel 56 is preferably blocked at 58.

The outer shell 52 includes a plurality of perforations 59 which are of the same size and formed in the same manner as the perforations 26 previously described with regard to FIG. 7.

The annular fluid supply channel 56 is communicated with fluid source 60 through conduit 62.

A substantial portion 64 of the length of trocar 48 is covered with the perforations 59 so as to define an operative zone 64 of the trocar 48 which will be in contact with the patient's tissue when the trocar 48 is inserted through the incision in the patient's outer skin.

The trocar 48 thus provides a means for bathing the exposed tissue at the incision site in the flushing fluid 66.

Preferably the flushing fluid 66 includes toxic solutions and/or anti-adhesive solutions as previously described.

Additionally, the outer surface 68 of outer shell 52 may be permanently coated with cytotoxic and/or anti-adhesive materials as previously described.

Thus it is seen that the apparatus and methods of the present invention readily achieve the ends and advantages mentioned as well as those inherent therein. While certain preferred embodiments of the invention have been illustrated and described for the purposes of the present disclosure, numerous changes in the arrangement and construction of parts and steps may be made by those skilled in the art, which changes are encompassed within the scope and spirit of the present invention as defined by the appended claims.

What is claimed:

1. A surgical apparatus for reducing cancer cell transportation when the apparatus is used to operate on cancerous tissue, comprising:

an instrument having an operative zone defined thereon for physical engagement with a patient's body tissue, the instrument having a foraminous rigid outer shell disposed in the operative zone, the foraminous rigid outer shell having a plurality of perforations defined therein, wherein the perforations each have a diameter less than one-hundredth of a minimum cross sectional diameter of the operative portion of the instrument, the instrument having a fluid supply channel defined therein the supply channel being in fluid communication with the perforations for diffusing a flushing fluid out the perforations throughout the operative zone, so that adhesion of tissue to the operative zone of the instrument is reduced;

a fluid supply source communicated with the fluid supply channel for supplying flushing fluid to the fluid supply channel at a pressure; and wherein the perforations have a size and density and the pressure is sufficient to dislodge a majority of otherwise adhered tissue from the outer shell and to thereby reduce cancer cell transportation when the instrument is used to operate on cancerous tissue.

2. The apparatus of claim 1, wherein the perforations are uniformly distributed over the operative zone of the instrument.

3. The apparatus of claim 1, wherein the perforations each have a diameter of no greater than 100 microns.

4. The apparatus of claim 3, wherein the perforations are laser drilled holes.

5. The apparatus of claim 1, further comprising:

the fluid supply source containing a toxic fluid which kills cancerous cells.

6. The apparatus of claim 5, wherein the toxic fluid includes iodine.

7. The apparatus of claim 1, further comprising:

the fluid supply source containing an anti-adhesive surfactant solution which reduces adhesion of tissue to the outer shell of the instrument.

8. The apparatus of claim 7, wherein the anti-adhesive surfactant solution includes RGD peptide.

9. The apparatus of claim 1, wherein:

the instrument is a trocar, the outer shell is a cylindrical shell, and the supply channel is an annular supply channel communicated with a cylindrical inner surface of the cylindrical shell.

10. The apparatus of claim 9, wherein:

the operative zone has a length sufficient to span a puncture wound in the patient's outer tissues.

11. The apparatus of claim 1, wherein the instrument is a laparoscopic surgical instrument of a size which can be inserted through a trocar having a diameter of no more than twelve millimeters.

12. The apparatus of claim 1, further comprising a cytotoxic coating on the operative zone of the instrument.

13. The apparatus of claim 12 wherein the cytotoxic coating includes iodine.

14. The apparatus of claim 1, further comprising an anti-adhesive coating on the operative zone of the instrument.

15. The apparatus of claim 14, wherein the anti-adhesive coating includes tetrafluroethylene fluorocarbon polymer.

* * * * *